United States Patent [19]

Hiki et al.

[11] Patent Number: 5,499,630
[45] Date of Patent: Mar. 19, 1996

[54] CATHETER TYPE ULTRASOUND PROBE

[75] Inventors: Susumu Hiki, Otawara; Mituo Kondo; Kenji Abe, both of Omiya, all of Japan

[73] Assignees: Kabushiki Kaisha Toshiba, Kawasaki; Fuji Photo Optical Co. Ltd., Omiya, both of Japan

[21] Appl. No.: 346,172

[22] Filed: Nov. 22, 1994

[30] Foreign Application Priority Data

Nov. 22, 1993 [JP] Japan .................................. 5-313962

[51] Int. Cl.⁶ ...................................................... A61B 8/12
[52] U.S. Cl. ...................................... 128/662.05; 600/104
[58] Field of Search ........................... 128/751, 753–754, 128/662.05, 662.06; 600/104–105

[56] References Cited

U.S. PATENT DOCUMENTS

| | | | |
|---|---|---|---|
| 2,708,437 | 5/1955 | Hutchins | 600/104 |
| 3,918,439 | 11/1975 | Zimmer | 600/104 |
| 4,742,829 | 5/1988 | Law et al. | 128/662.05 |
| 4,763,662 | 8/1988 | Yokoi | 128/662.05 |
| 5,261,889 | 11/1993 | Laine et al. | 600/104 X |
| 5,345,940 | 9/1994 | Seward et al. | 128/662.06 |

*Primary Examiner*—Francis Jaworski
*Attorney, Agent, or Firm*—Oblon, Spivak, McClelland, Maier & Neustadt

[57] ABSTRACT

An ultrasound probe with a needle guide passage for a puncture needle, the ultrasound probe having an ultrasound transducer mounted on a girder portion of a rigid fore end section at the distal end of a flexible insert section of a catheter member to be introduced into an intracavitary portion, and a needle passage provided axially within the catheter member for launching the puncture needle therethrough. The needle passage is turned toward an exit opened on a lateral side portion of the rigid fore end section at a position on the near side of the ultrasound transducer. The rigid fore end section of the catheter member is provided with a bent portion which is turned off the axis of the catheter member through a predetermined angle in a direction away from a needle launching direction of the needle passage at a position on the near side of the exit opening of the needle passage.

3 Claims, 5 Drawing Sheets

CATHETER TYPE ULTRASOUND PROBE

BACKGROUND OF THE INVENTION

1. Field of the Art

This invention relates to a catheter type ultrasound probe with an ultrasound transducer at the distal end of a catheter member for intracorporeal inspections or examinations, and more particularly to a catheter type ultrasound probe which is equipped with a puncture needle with improved penetration characteristics.

2. Prior Art

Ultrasound examination systems are generally arranged to transmit ultrasound pulses into an intracorporeal portion of interest from an ultrasound transducer element while receiving and processing return echo signals to produce video signals of tomographic ultrasound images for display on a monitor screen. The known ultrasound examination systems include the so-called catheter type ultrasound probe having an ultrasound transducer element mounted at the distal end of a narrow catheter member to be inserted into an intracorporeal portion to be examined. In case a diseased portion is spotted by an ultrasound examination, it is the general practice to use a puncture needle for various purposes, for example, for injecting a medicine into the diseased portion, for injecting contrast media for closer examination, for sampling tissues from the diseased portion, or for drainage. The puncture needle of this sort usually has a hollow body which is sharp-pointed at its fore end to penetrate a targeted intracorporeal portion to a predetermined depth. In such a puncturing operation, a puncture needle is directed toward a diseased portion or other target portion which needs a treatment, confirming the needle position by way of an ultrasound image which is displayed on a monitor screen.

Naturally, some catheter type ultrasound probes are constructed to permit the use of a puncture needle of the sort as mentioned above, the puncture needle being launched through a needle guide passage which is provided on a catheter member of the ultrasound probe. In this regard, the operation of needle penetration into a diseased portion is likewise monitored through ultrasound images displayed on a monitor screen of an ultrasound image observation terminal of the examination system. Therefore, the puncture needle should always be within the view field of the ultrasound image under observation. The view filed in the ultrasound image observation is produced by an ultrasound scanning operation, for example, by a B-mode scanning operation in a linear or convex scanning mode under either mechanical or electronic drive. For instance, for an electronic linear or convex scanning operation, a large number of transducer elements which constitute the ultrasound transducer are arrayed in a row on lateral side portions of a tip end portion of the catheter member of the probe to take a view field in a direction perpendicular to the axis of the catheter member. A puncture needle therefore needs to be launched into the view field of the ultrasound image under observation from a position on the near side of the ultrasound transducer. For this purpose, the needle guide passage which guides the puncture needle along the axis of the catheter member is turned through an obliquely curved passage toward an exit which is opened on a lateral side portion of the catheter member at a position on the near side of the ultrasound transducer.

In this connection, from the standpoint of protection of patients and higher target hitting characteristics, the puncture needle point Should preferably be driven out of the needle passage in such a way as to penetrate a target or diseased portion from as close a position as possible through an intracavitary wall, and from a needle guide passage which is as short as possible in length. To this end, attempts have been made to project a needle point from an exit which is opened at a position close to the ultrasound transducer. For instance, in case of driving a puncture needle into the pancreas through a stomach wall from a needle passage on a catheter member which has been inserted into the stomach, it has been considered that the optimum needle launching angle relative to the axis of the catheter member is 30°. This means that the axial needle passage has to be arranged to turn its direction by approximately 30° toward its exit through a curved needle passage to comply with the optimum needle launching angle.

Further, considering the thrust which is required to drive a puncture needle for penetration into a diseased portion through an intracavitary wall, the puncture needle is preferred to be formed of a hard rigid material at least in its projectile portion to be launched from the needle passage. However, with a needle body of high rigidity, it is difficult to switch the needle direction at an angle as large as 30°. In this regard, the conventional procedure has been to resort to a flexible needle which can easily bend itself through such an angle for a turn toward the exit opening of the needle passage, sacrificing to some extent the thrust for the needle penetration through intracavitary walls.

SUMMARY OF THE INVENTION

In view of the foregoing situations, it is a primary object of the present invention to provide an ultrasound probe which is capable of launching a puncture needle smoothly through and from a needle passage within a catheter member of the probe in such a way as to ensure improved penetration into targeted intracorporeal portions in various puncturing operations.

In accordance with the present invention, the above-stated objective is achieved by the provision of an ultrasound probe with a needle guide passage for a puncture needle, the ultrasound probe comprising: an ultrasound transducer mounted on a girder portion of a rigid fore end section at the distal end of a flexible catheter member of the ultrasound probe; and a needle passage provided axially within the catheter member of the ultrasound probe for launching the puncture needle therethrough, the needle passage being turned toward an exit opened on a lateral side portion of the rigid fore end section at a position on the near side of the ultrasound transducer, the rigid fore end section of the catheter member being provided with a bent portion which bent portion being turned off the axis of the catheter member through a predetermined angle in a direction away from a needle launching direction of the needle passage at a position on the near side of the exit opening of the needle passage.

For example, in order to project a puncture needle into the view field of an ultrasound transducer which is held against a stomach wall portion for monitoring the needle penetration as described hereinbefore, it suffices to project the needle at a certain angle relative to the active surface of the ultrasound transducer. Namely, there is no necessity for projecting the puncture needle at a predetermined angle relative to the axis of the insert portion itself. According to the present invention, a rigid fore end section of the catheter member of the ultrasound probe is bent through a predetermined angle at a position on the near side of the ultrasound transducer and within the length of a needle passage portion on the rigid fore end section, thereby permitting to project the puncture needle at a smaller angle and, depending upon the angle of the bent portion of the rigid fore end section, to project the needle substantially in a straight forward direction from the needle passage. Therefore, there is no necessity any longer for forcibly bending the hollow needle body as it is led out through the exit opening of the needle passage, and it becomes possible to employ a puncture needle of higher rigidity or stiffness for the purpose of securing sufficient thrust for the needle penetration and improved needle control or drivability in puncturing operations.

The catheter member of the ultrasound probe is required to be flexible enough to bend itself along the path of insertion into an intracavitary portion to be examined, so that its body is mostly formed of a soft flexible material except a fore end portion with a rigid structure which serves as a support for the ultrasound transducer and provides an opening through which a puncture needle is to be launched. Besides, in some cases catheter type ultrasound probes are arranged as an ultrasound endoscope with endoscopic observation means including illumination and observation windows. An ultrasound endoscope of this sort necessarily has a hard rigid support structure of an increased length at the fore end of the catheter member. In this regard, for example, in a case where an ultrasound endoscope is used for examination or diagnosis of the digestive system, the path of insertion of the catheter member into the digestive tract contains a turn or bend of the largest angle at the throat portion where normally a lengthy rigid fore end section at the distal end of an ultrasound catheter cannot be passed without causing extremely great pains to the patient. However, when the rigid support structure at the distal end of the ultrasound catheter member is partly bent at a predetermined angle as described above, it becomes possible to pass the rigid section smoothly along the angular turn at the throat without causing much pains to the patient by turning the angularly bent portion of the rigid fore end section to lie in the same direction as the angular turn of the path at the throat. Past the throat portion, the catheter member enters the esophagus which is a tract of substantially elliptic shape in section, so that the catheter is allowed to go down through the esophagus without meeting any hindrance by turning the bent portion of the rigid fore end section in the direction of the longer side of the elliptic tract.

Further, as soon as the catheter member is introduced into the stomach or other organs for examination or diagnostic purposes, the ultrasound transducer at the fore end of the catheter member is actuated to transmit ultrasound pulses toward internal tissues through an intracavitary wall. At this time, the ultrasound transducer needs to be held in intimate contact with the intracavitary wall. However, in case a balloon is used, there is no need for holding the ultrasound transducer in intimate contact with the intracavitary wall, although at least it has to be positioned in properly facing relationship with the intracavitary wall. In this regard, an ultrasound transducer which is mounted on a bent fore end portion of the catheter member can be brought into intimate contact with or into properly confronting relation with an intracavitary wall extremely easily.

The above and other objects, features and advantages of the invention will become apparent from the following description taken in conjunction with the accompanying drawings which show a preferred embodiment of the invention by way of example.

DESCRIPTION OF PREFERRED EMBODIMENTS

Figure 1:
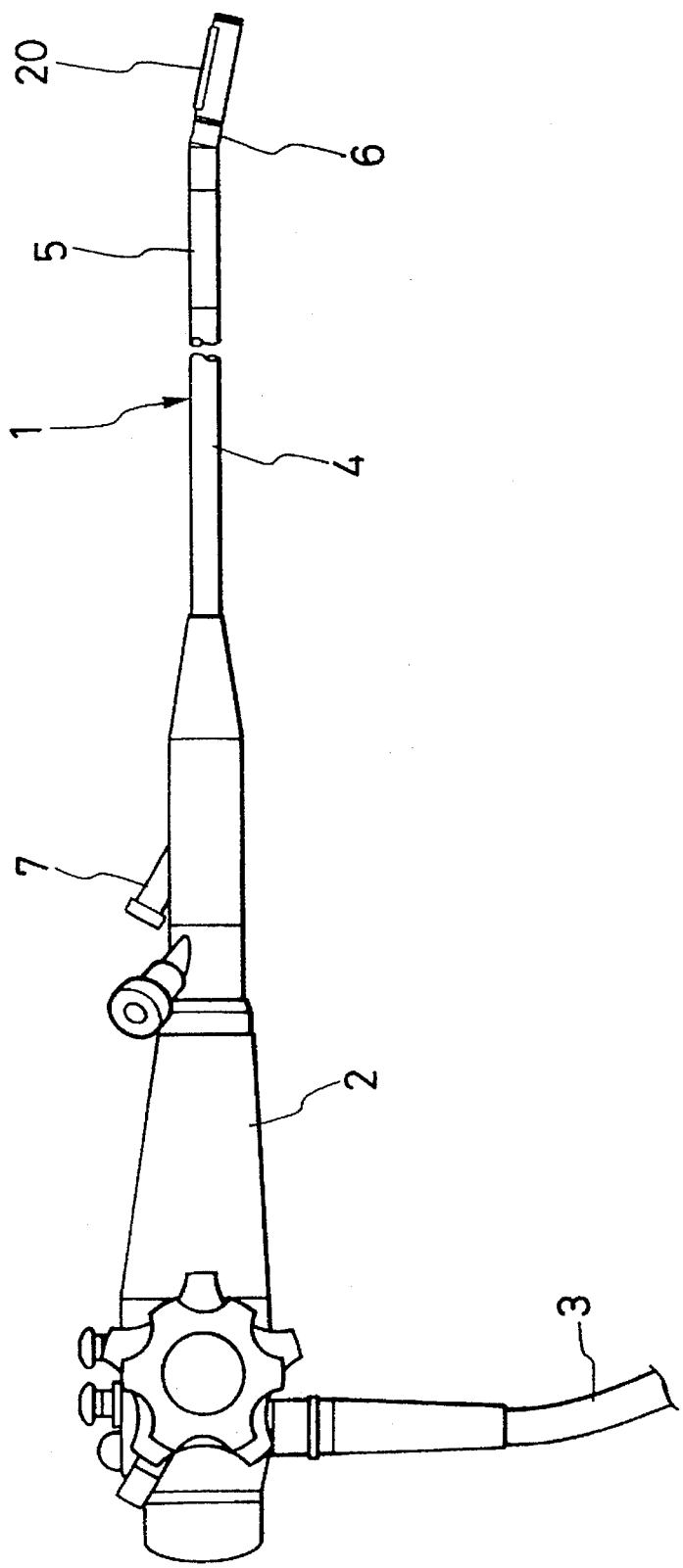
FIG. 1 is a schematic illustration showing the general arrangement of a catheter type endoscopic ultrasound probe as an embodiment of the ultrasound probe according to the invention.

Hereafter, the invention is described more particularly by way of an embodiment shown in the drawings. The ultrasound probe shown in the drawings is arranged as an endoscopic ultrasound probe, which however is not necessarily required to include endoscopic observation means.

FIG. 1 shows the general arrangement of the ultrasound endoscope system including a catheter member 1, an operating unit 2 and a universal cable 3. Except a proximal end portion which is connected to the operating unit 2, the catheter member 1 is mostly constituted by a soft flexible section 4 which can bend itself along a path of insertion, and successively provided with an angle section 5, which is connected to the fore end of the flexible section 4, and a rigid fore end section 6 which is connected to the fore end of the angle section 5.

Figure 2:
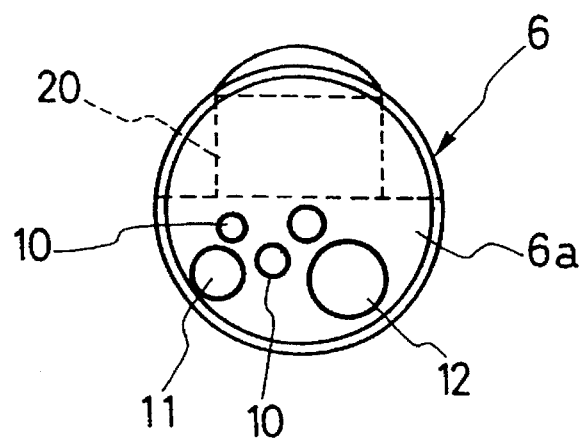
FIG. 2 is a front view of a fore end portion of a catheter member.
Figure 3:
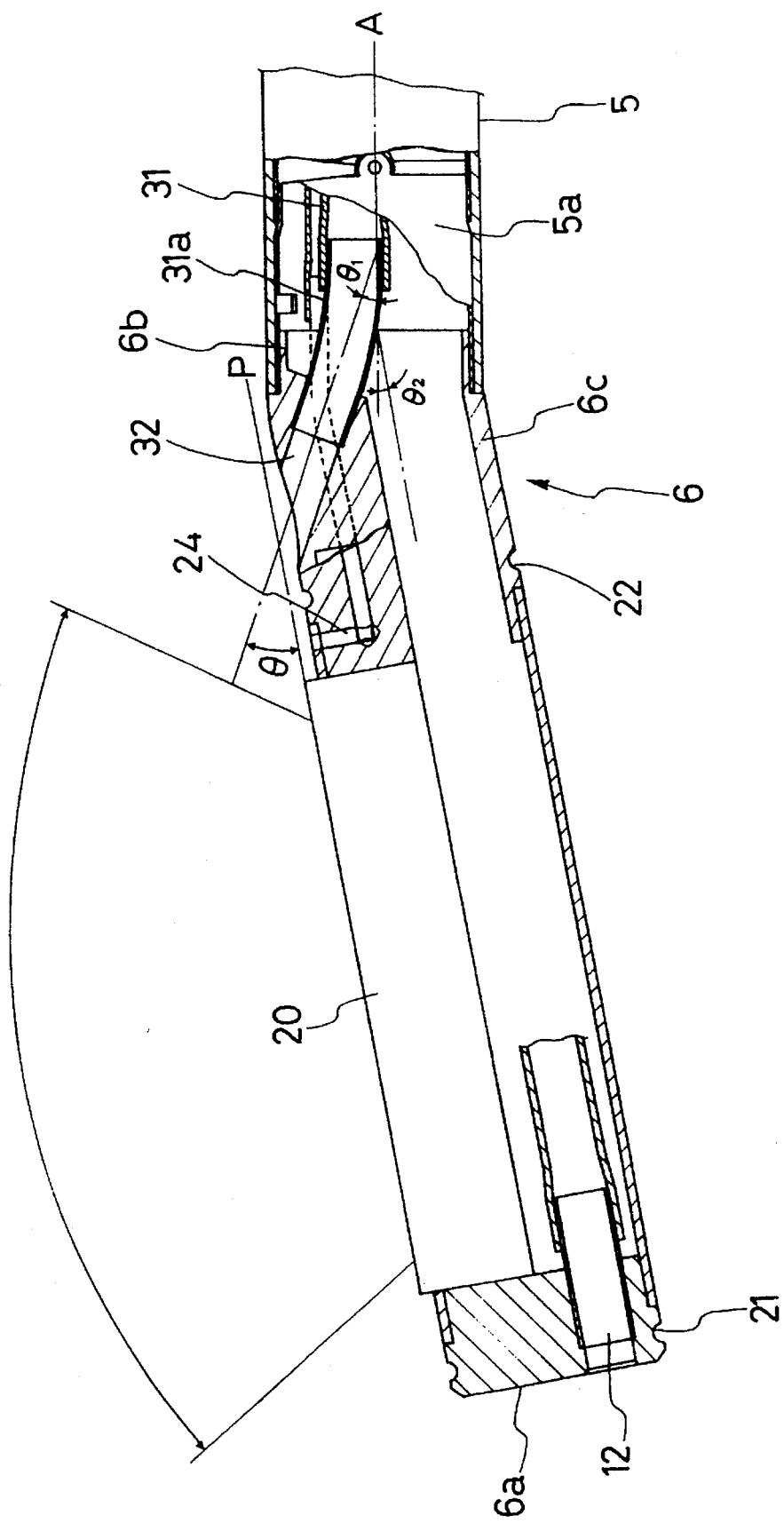
FIG. 3 is a longitudinal section of the fore end portion of the catheter member.

As shown in FIGS. 2 and 3, the rigid fore end section 6 is provided with endoscopic observation means 11 on its distal end face 6a including an illumination window 10 and an observation window 11. Disposed in the illumination window 10 is a light emitting end of a light guide. An objective lens is fitted in the observation window 11 to form an optical image at a predetermined plane where a solid-state image sensor (the light incident end of an image guide in case of an optical endoscope) is located to take out the images for the endoscopic observation after conversion into electric signals through the solid-state image sensor. Further, a biopsy channel 12 is opened on the distal end face 6a to protrude forceps or other instruments therethrough. These endoscopic observation means and biopsy channel 12 are arranged in a known manner, and therefore detailed description in this regard is omitted for the sake of simplicity of explanation.

Mounted on the rigid fore end section 6 on the near side of the endoscopic observation means is an ultrasound transducer 20 which is constituted, for example, by a large number of transducer elements arrayed in a row in the axial direction of the rigid fore end section 6 for electronic convex scanning (or linear scanning). The view field which is available from this ultrasound probe arrangement is indicated by arrows in FIG. 3. Formed on the front and rear sides of the ultrasound transducer 20 are annular grooves 21 and 22 in which opposite ends of a balloon 23 (FIG. 5) in the form of a tubular thin film of elastic material are fixedly anchored by the use of rubber rings or the like. A nozzle 24 is opened at a position between the ultrasound transducer 20 and the groove 22 to supply an ultrasound transmissive medium like deaerated water for inflation of the balloon 23.

Figure 4:
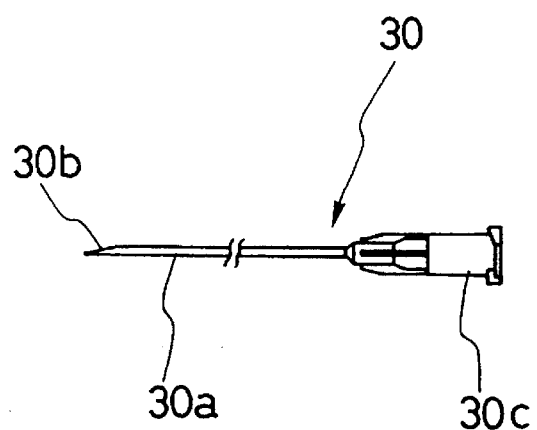
FIG. 4 is a schematic illustration showing the general construction of a puncture needle.

Indicated at 30 in FIG. 4 is a puncture needle 30 having a hollow needle body 30a which is sharp-pointed at its fore end 30b. The puncture needle 30 is introduced into a needle passage 31, which extends from a needle entrance 7 on the operating unit 2 to the rigid fore end section 6, the flexible tubular body of the catheter member 1 and the angle section 5, and launched out of an exit 32 which is opened on a lateral side portion of the rigid fore end section 6. The base end of the puncture needle 30 is formed into an enlarged coupling end 30c which is connectible to a member which supplies or sucks a medicinal or other liquid to and from the puncture needle 30.

The needle passage 31 is constituted by a flexible tube which is extended in the axial direction between the flexible section 4 and the angle section 5. In the rigid fore end section 6, it is constituted by a curved passage 31a of a hard tube which is turned through a predetermined angle to direct the needle passage toward the exit opening 32 on a lateral side of the rigid fore end section 6. Besides, the rigid fore end section 6 itself is bent through a predetermined angle in a direction away from the curved needle passage portion 31a at an intermediate position within the length of the curved needle passage portion 31a. Namely, the rigid fore end section is constituted by an axial straight portion 6b which is connected to the angle portion 5 and a bent portion 6c which is bent at a predetermined angle with the axis of the straight portion 6b. The above-described ultrasound transducer 20 and the endoscopic observation means including the illumination and observation windows 10 and 11 are mounted on the bent portion 6c. Accordingly, when the angle of the turn of the curved needle passage 31a toward its exit opening 32 is $\theta_1$ relative to the axis of the catheter 1 and the angle between the straight portion 6b and bent portion 6c of the rigid fore end portion is $\theta_2$, the puncture needle 30 is launched out of the needle passage 31 at an angle of $\theta_1+\theta_2=\theta$ relative to the plane (P) of the ultrasound transducer 20.

In this connection, the rigid fore end section 6 is located forward of and fixedly connected to an angle ring 5a in the foremost position of the angle rings which constitute the angle section 5. However, in angling operations to bend the rigid fore end section in a particular direction, the foremost angle ring 5a remains as an inflexible part relative to the straight portion 6b of the rigid fore end section 6, so that it can be regarded substantially same as and part of the straight portion 6b from a structural point of view.

With the above-described endoscopic ultrasound probe according to the invention, for example, the catheter 1 is introduced into the digestive tract down to the stomach through the throat and esophagus to make an intra-gastric examination by the use of the endoscopic observation means. If necessary, the puncture needle 30 can be penetrated into the pancreas through an intra-gastric wall for injection of a medicine or contrast medium or for drainage.

Figure 5:
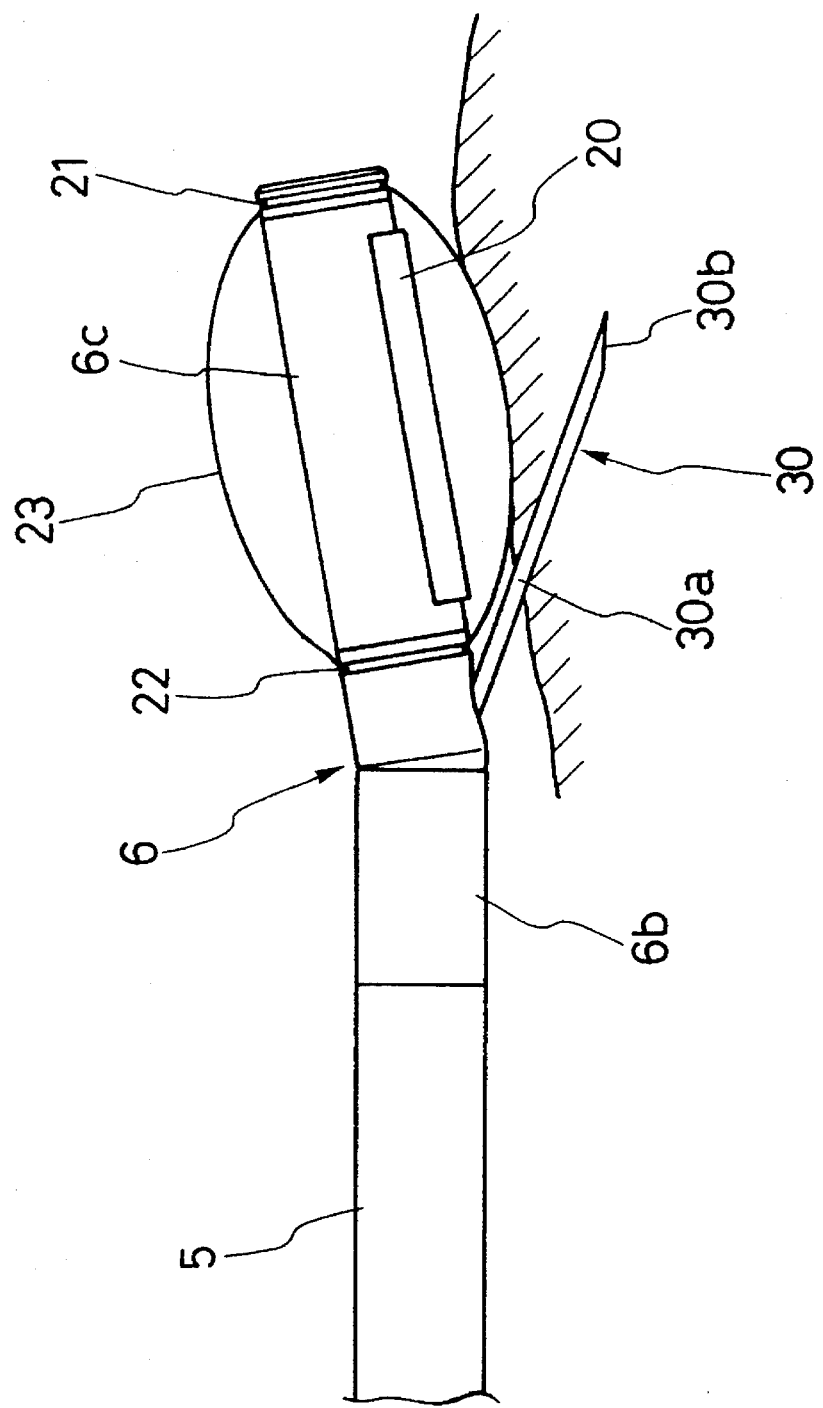
FIG. 5 is a schematic illustration explanatory of a puncturing operation by the puncture needle.

On such an occasion, as shown in FIG. 5, the ultrasound transducer 20 is held in intimate contact with an intracavitary wall, or properly faced toward an intracavitary wall through a balloon 23 which has been set in position between the grooves 21 and 22 (both of which are located on the bent portion 6c of the rigid fore end section 6) and inflated into intimate contact with the intracavitary wall by supply of an ultrasound transmissive medium from the nozzle 24. In this position, ultrasound pulses are transmitted toward the intracavitary wall from the ultrasound transducer 20 while received echo signals are sent to the ultrasound image observation terminal and converted into video signals through predetermined signal processing operations to display ultrasound images on the monitor screen. No matter whether it is convex scanning or linear scanning, the ultrasound transducer 20 has to be positioned parallel with the intracavitary wall directly or through the balloon 23 in order to display ultrasound images properly on the monitor screen.

The catheter member 1 is substantially rigid from the tip end of the rigid fore end section 6 to the foremost ring 5a of the angle section 5. However, the rigid section on which the ultrasound transducer 20 is mounted is bent by an angle of $\theta_2$ relative to the axis of the catheter 1 as a whole, so that the ultrasound transducer 20 can be pressed uniformly against an intracavitary wall by pushing the catheter 1 thereagainst straight from the direction of $\theta_2$. In addition, angular adjustments can be made by flexing the angle section 5 if necessary, thereby permitting to reposition the ultrasound transducer 20 properly relative to the intracavitary wall in an extremely facilitated manner.

In this state, while looking at the ultrasound image which is displayed on the monitor screen, the puncture needle 30 is launched to penetrate through an intracavitary wall into a target portion which needs a therapeutic treatment or examination. For this purpose, the puncture needle 30 is driven out of the exit opening 32 of the needle passage 31 within the catheter 1 through the curved passage 31a to let the needle point 30b penetrate to a target depth through the intracavitary wall. In this instance, in order to get the needle point 30b to a target point smoothly in a secure manner, the thrust force which is applied to the needle body 30a has to be transmitted down to the needle point 30a in a sufficient degree. In this regard, due to the flexibility of the catheter 1 which contains the flexible section 4 and the angle section 5, it may be difficult to form the puncture needle body 30a from a hard rigid pipe as used in percutaneous puncture. Nevertheless, the puncture needle body 30a should have a certain degree of stiffness and rigidity, although a needle body of high rigidity material might deteriorate the needle maneuverability and passability through the needle passage 31 in needle launching operations. Especially, in case the needle passage 31 which runs in the axial direction of the catheter 1 is turned at a large angle toward the exit opening 32, its passage through the angular turn would become extremely difficult.

In this connection, as described hereinbefore, the rigid fore end section 6 is constituted by the axial straight portion 6b and the bent portion 6c which is bent by an angle of $\theta_2$ from the straight portion 6b and in a direction away from the curved portion 31a of the needle passage 31, so that, in case the turn angle of the curved needle passage 31a is $\theta_1$ the puncture needle 30 can be launched at an angle of $\theta_1+\theta_2=\theta$. For instance, when it is required to launch the puncture needle 30 at an angle of 30° relative to the ultrasound transducer 20, the turn angle of the curved needle passage portion 31a can be suppressed to 20° by providing a bent portion 6c of 10°. This ensures smooth passage through the curved portion 31a even for a puncture needle 30 which is increased in rigidity to secure sufficient stiffness for efficiently propelling the needle point 30b to a target on application of a thrust on the needle body.

Figure 6:
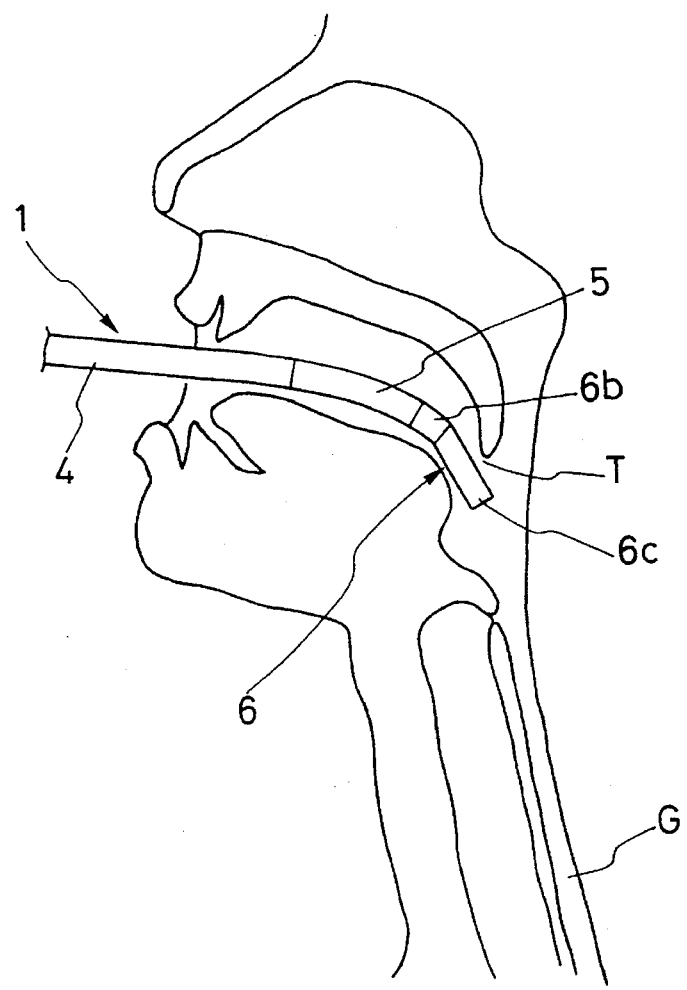
FIG. 6 is a schematic illustration explanatory of an intracavitary path of insertion of the catheter member.
Figure 7:
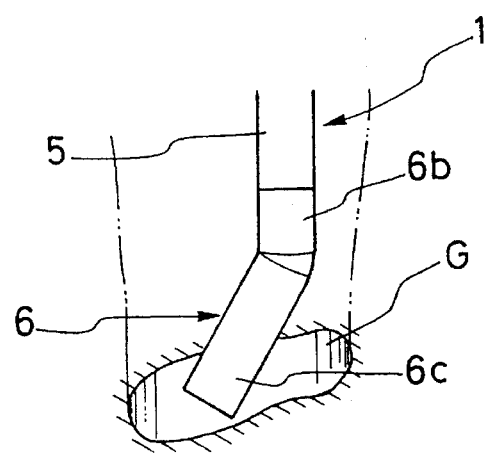
FIG. 7 is a schematic illustration of the catheter member being inserted through the esophagus.

Further, the provision of a bent portion in part of the rigid fore end section also contributes to facilitate the insertion of the catheter into an intracavitary portion of interest. Namely, as shown particularly in FIG. 6, in case of insertion into the digestive tract, the catheter has to be passed through the throat T where the path of insertion turns at a large angle. Therefore, with an endoscopic ultrasound probe which has a straight rigid fore end section of an increased length at the tip end of a catheter to accommodate endoscopic observation means in addition to an electronic scanning type ultrasound transducer 20, the straight rigid fore end section is met by considerable resistance on passage through the throat T to give great pains to the patient. In contrast, the rigid fore end section 6 with the bent portion 6c can be inserted smoothly through the throat T with far less pains on the part of the patient by introducing the catheter 1 in such a way that the bent portion 6c lie in the same direction as the bend in the path of insertion at the throat T. Past the throat T, the catheter is introduced into the esophagus G which is in the form of a flattened elliptic tube as shown in FIG. 7. Therefore, if the bent portion 6 is turned in the direction of the longer side in the elliptic canal, the catheter 1 can be moved down through the esophagus G substantially free of any resisting obstacles. Of course, within a broad intracorporeal cavity like the stomach, the existence of the bent portion at the tip end of the rigid fore end section 6 gives rise to no problems in particular. On the contrary, as described hereinbefore, it is advantageous in that the ultrasound transducer 20 can be easily brought into intimate contact or into a properly facing relation with an intracavitary wall of interest.

In the foregoing embodiment, the ultrasound probe of the invention has been described as an ultrasound probe for the upper digestive system in relation with an operation for puncturing the pancreas, with the puncture needle. Needless to say, the present invention is not limited to the particular examples shown. The same applies to the angles of the puncture needle and the bent portion relative to the ultrasound transducer. For example, in case the puncture needle is to be launched at as small an angle as 10° relative to the plane of the ultrasound transducer, it suffices to provide a straight needle passage on a catheter with a bent portion of 10° on its rigid fore end section. Moreover, the ultrasound probe of the present invention can be used with various ultrasound scanning systems such as convex, linear or radial scanning system, which may be of a mechanical type adapted to drive an ultrasound transducer mechanically within the rigid fore end section.

As described above by way of a preferred embodiment, the ultrasound probe according to the present invention is provided with a bent portion in the rigid fore end section of the ultrasound catheter, thereby permitting to moderate correspondingly the turn angle in the curved portion of the needle passage through which a puncture needle is to be launched. Therefore, even if a puncture needle of high rigidity is used for the purpose of transmitting a thrust force effectively to the needle point for securer penetration into a diseased or other target portion through an intracavitary wall, it becomes possible to ensure smooth passage of the puncture needle through the curved portion of the needle passage in addition to remarkable improvements in needle drivability. Besides, the bent portion which is provided on part of the rigid fore end section, which carries the ultrasound transducer, makes it easier to hold the ultrasound transducer in intimate contact with or in properly confronting relation with an intracavitary wall of interest. Further, when inserting the catheter along a path which contains a bend of a large angle as at the throat, the rigid fore end section can be smoothly passed around the bend in the path of insertion without causing much pains to the patient by turning the bent portion at the tip end of the rigid fore end section to lie in the same direction as the bend in the path of insertion.

What is claimed is:

1. An ultrasound probe with a needle guide passage for a puncture needle, said ultrasound probe comprising:

an ultrasound transducer mounted on a girder portion of a rigid fore end section at the distal end of a flexible insert section of a catheter member of said ultrasound probe; and a needle passage provided axially within said catheter member of said ultrasound probe for launching a puncture needle therethrough, said needle passage being turned toward an exit opened on a lateral side portion of said rigid fore end section at a position on the near side of said ultrasound transducer; and said rigid fore end section of said catheter member being provided with a bent portion which bent portion being turned off the axis of said catheter member through a predetermined angle in a direction away from a needle launching direction of said needle passage at a position on the near side of said exit opening of said needle passage.

2. An ultrasound probe as defined in claim 1, wherein an angle section is interposed between said flexible section and rigid fore end section of said catheter member for angling said rigid fore end section in a desired direction relative to the axis of said flexible section.

3. An ultrasound probe as defined in claim 1, wherein said rigid fore end section of said catheter member is provided with endoscopic observation means in addition to said ultrasound transducer, said endoscopic observation means including an illumination window and an optical observation window with an objective lens.

* * * * *